US006307063B1

(12) United States Patent
Sullivan

(10) Patent No.: US 6,307,063 B1
(45) Date of Patent: Oct. 23, 2001

(54) CONVERSION OF COMPOUNDS OF TITANIUM IN A PLUS 4 OXIDATION STATE TO TITANIUM COMPOUNDS IN A PLUS 3 OXIDATION STATE

(75) Inventor: Jeffrey M. Sullivan, Loveland, CO (US)

(73) Assignee: Boulder Scientific Company, Mead, CO (US)

(*) Notice: Subject to any disclaimer, the term of this patent is extended or adjusted under 35 U.S.C. 154(b) by 0 days.

(21) Appl. No.: 09/784,736

(22) Filed: Feb. 15, 2001

(51) Int. Cl.$^7$ .................. C07F 17/00; C07F 3/00
(52) U.S. Cl. .............. 549/208; 549/210; 556/54; 556/56
(58) Field of Search .................. 549/208, 210; 556/54, 56

(56) References Cited

U.S. PATENT DOCUMENTS

| 5,264,590 | * | 11/1993 | Strickler | 549/208 |
| 5,367,085 | * | 11/1994 | Strickler | 549/206 |
| 6,093,833 | * | 7/2000 | Kershner | 549/210 |

* cited by examiner

Primary Examiner—Porfirio Nazario-Gonzalez
(74) Attorney, Agent, or Firm—Edward S. Irons

(57) ABSTRACT

The reduction of a titanium tetrahalide with titanium in the presence of an ether which forms an adduct with titanium trihalide, wherein an adduct insoluble in said ether is produced.

18 Claims, No Drawings

CONVERSION OF COMPOUNDS OF TITANIUM IN A PLUS 4 OXIDATION STATE TO TITANIUM COMPOUNDS IN A PLUS 3 OXIDATION STATE

FIELD OF THE INVENTION

This invention relates to the conversion of compounds of titanium in a plus 4 (IV) oxidation state to similar compounds in which titanium is in a plus 3 (III) oxidation state.

More particularly, the invention relates to the reduction of $TiCl_4$ with particulate titanium in the presence of an ether which forms a $TiCl_3$ complex insoluble in the reaction medium.

BACKGROUND OF THE INVENTION

It is known to reduce $TiCl_4$ ether complexes pre-formed in the same pot or made during the reduction reaction with aluminum or magnesium powders, aluminum ribbon, alkyls, hydrides and lithium alkyls.

U.S. Pat. No. 6,093,833 describes a process for producing a trivalent titanium coordination complex by the reduction of a Ti(IV) salt. The process comprises the steps of (a) forming a complex by adding a stoichiometric excess of an ether to a Ti(IV) salt, and then (b) reducing the complex with a metal powder, specifically a magnesium or an aluminum powder, which forms a soluble magnesium or aluminum chloride complex by-product in the ether medium.

Also, the $TiCl_3$.adduct produced is contaminated with small amounts of magnesium halide or aluminum halide salts.

SUMMARY OF THE INVENTION

This invention provides a method for converting a Ti(IV) compound to a complex of a Ti(III) compound. The complex is free of foreign metal contaminations. A preferred embodiment of the invention entails the treatment of $TiCl_4$ in the presence of an ether, preferably tetrahydrofuran or dimethoxyethane, with particulate titanium metal to form a high yield of a $TiCl_3$.ether complex.

GENERAL DESCRIPTION OF THE INVENTION

In general, the invention may include reducing a Ti(IV) compound with particulate Ti, wherein a corresponding Ti(III) compound is produced. The reaction is conducted in the presence of an ether reactant which forms a coordination complex with the Ti(III) compound.

The invention is illustrated by generic equation 1:

Equation 1

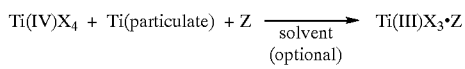

wherein the mesh size of the particulate titanium is not more than about 100, X is a monovalent anion, preferably a halogen, and Z is an ether which forms a $TiCl_3$ complex insoluble in the reaction medium. The optional solvent is preferably an aromatic hydrocarbon, e.g., toluene. The reaction is preferably conducted by reflux at 90–100° C. for about 4 to 7 hours.

Titanium metal is oxidized to Ti(III), and Ti(IV) is reduced to Ti(III) giving a product free of contamination from other metal halides.

EXAMPLE 1

Preparation of $TiCl_3$.3THF

This example illustrates one embodiment of the invention as shown by equation 1 in the Ti(IV) compound is $TiCl_4$, in which the $TiCl_3$ complex-forming reactant is THF and in which the solvent is toluene. The reaction is illustrated by equation 2:

Equation 2

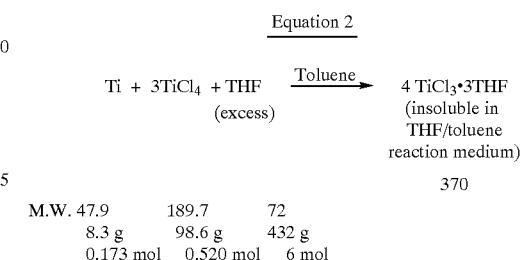

A 2 L round bottom flask (equipped with a thermometer, mechanical stirrer, and reflux condenser) was charged with particulate titanium (~100 mesh, 99.9 purity, 8.3 g), titanium tetrachloride (98.6 g) and toluene (800 g). THF (432 g) was added with ice cooling, while the pot temperature was maintained between 10–20° C. The reaction mixture was heated to reflux (90–100° C.) for 6 hours. The reaction mixture was then cooled to room temperature and filtered. The solid $TiCl_3$.3THF product was washed with deoxygenated hexane (200 mL) and dried in vacua. Yield=240 g; 94%, based on total charge of titanium (both $TiCl_4$ and particulate titanium).

EXAMPLE 2

Preparation of $TiCl_3$.1.5 DME

This example illustrates an embodiment of the invention in which $TiCl_4$ is converted to $TiCl_3$.1.5 DME in the absence of a solvent.

Equation 3

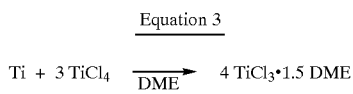

Charge flask with particulate titanium (~100 mesh, 0.25 mole, 11.9 g) and DME (2 kg). With cooling slowly, add titanium tetrachloride (0.77 mole, 146.3 g), maintaining temperature at 0° C. After addition is complete, slowly warm to reflux, and hold at reflux for 8 hours. Cool to room temperature and filter; then dry in vacua. Yield=246 g; 85%, based on total charge of titanium (both $TiCl_4$ and particulate titanium).

Analysis:
Ti=16.6%
Cl=36.6%
Theoretical:
Ti=16.5%
Cl=36.7%

Product is aluminum and magnesium free.

As illustrated by Examples 1 and 2, the reduction reaction may be conducted in a medium optionally comprising the complex-forming ether per se or in combination with any non-interfering solvent. Suitable solvents include aliphatic and aromatic hydrocarbons; aromatic hydrocarbons are preferred.

Compounds which form a complex with Ti(III) compounds are known. See German patent application DE 197

39 946 A1 published Mar. 18, 1999. Each such complex forming compound which yields a Ti(III) complex insoluble in the reduction reaction mixture is useful in this invention. Preferred complex-forming compounds are ethers, typically tetrahydrofuran (THF) and dimethoxyethane (DME).

Another aspect of the invention may include conversion of the Ti(III) products to metallocenes useful as olefin polymerization catalyst ligands, as olefin polymerization catalysts per se or as components of olefin polymerization catalyst systems.

I claim:

1. The method which comprises treating a titanium tetrahalide with particulate titanium in the presence of an ether which forms an adduct with titanium trichloride
    wherein a reaction mixture containing a complex of a titanium trihalide and said ether is produced, and
    wherein said treating is conducted in a medium in which said complex is insoluble.

2. The method of claim 1 wherein said treating is conducted in said ether.

3. The method of claim 1 or claim 2 wherein said treating is conducted in a medium comprising said ether and a non-interfering medium.

4. The method of claim 1 or claim 2 wherein said treating is conducted in a medium comprising an aromatic hydrocarbon.

5. The method of claim 1 or claim 2 wherein said ether is tetrahydrofuran or dimethoxyethane.

6. The method of claim 1 or claim 2 in which the mesh size of said particulate titanium is less than 100.

7. The method which comprises:
    (i) providing a reactor containing a titanium tetrahalide, and particulate titanium, and
    (ii) adding an ether which forms a complex with titanium trihalide to the contents of said reactor,
        wherein a reaction mixture containing a complex of a titanium trihalide and said ether is produced, and
        wherein said complex is insoluble in said reaction mixture.

8. The method of claim 7 wherein said titanium tetrahalide is titanium tetrachloride.

9. The method of claim 8 wherein said ether is tetrahydrofuran or dimethoxyethane.

10. The method for preparing a complex of a titanium trihalide and an ether which comprises:
    (i) providing a mixture of a titanium tetrahalide, particulate titanium, and a non-interfering medium in a reactor,
    (ii) adding an ether which forms a complex with titanium trihalide to said step (i) mixture in said reactor
        wherein an exothermic reaction occurs and a first reaction mixture is produced, and
        wherein the pot temperature in said reactor is maintained between about 10° C. and about 20° C. during said addition of said ether to said mixture in said reactor, and
    (iii) thereafter raising the temperature of said first reaction mixture in said reactor to about 90° C. to 100° C., and
    (iv) refluxing said first reaction mixture in said reactor at about 90° C. to 100° C.
        wherein a second reaction mixture containing an adduct of said ether and a titanium trihalide is produced in said reactor.

11. The method of claim 10 wherein said titanium tetrahalide is titanium tetrachloride.

12. The method of claim 10 wherein said ether added in step (ii) is THF or DME.

13. A method which comprises:
    (i) providing a mixture of $TiCl_4$, particulate titanium metal and toluene in a chilled reactor,
    (ii) adding tetrahydrofuran or dimethoxyethane to said step (i) mixture in said reactor wherein an exothermic reaction occurs,
    (iii) maintaining the pot temperature of said reactor at about 10° C. to 30° C. for the substantial duration of said exothermic reaction and thereafter raising said pot temperature to reflux temperature,
    (iv) refluxing said first reaction mixture for at least about four hours
        wherein a second reaction mixture comprising a $TiCl_3$.tetrahydrofuran complex or a $TiCl_3$.dimethoxyethane complex and toluene is produced, and
    (v) recovering said complex from said step (iv) second reaction mixture.

14. The method of claim 13 further comprising a step
    (vi) converting said adduct recovered in step (v) to a titanocene or a titanocene ligand.

15. A method which consists essentially of
    (i) treating titanium tetrachloride with particulate titanium in the presence of an ether which forms an adduct with titanium trichloride
        wherein a reaction mixture containing a complex of titanium trichloride and said ether is produced, and
        wherein said treating is conducted in a medium in which said adduct is insoluble;
    (ii) separating said adduct from said reaction mixture; and
    (iii) washing and drying said separated adduct
        wherein a titanium trichloride ether adduct free of contamination with halides of metals other than titanium is produced.

16. The method of claim 15 wherein said ether is dimethoxymethane or tetrahydrofuran.

17. A titanium trichloride adduct of dimethoxymethane or tetrahydrofuran free of contamination with halides of metals other than titanium wherein said adduct is produced by the method of claim 15 or claim 16.

18. A method of claim 15 or claim 16 further comprising a step
    (iv) converting said adduct washed and dried in step (iii) into a titanocene or a titanocene ligand.

* * * * *